(12) United States Patent
Day et al.

(10) Patent No.: US 11,617,512 B2
(45) Date of Patent: Apr. 4, 2023

(54) PROBE WITH A REMOVABLE TIP (71) Applicants: The University of Bristol, Bristol (GB); GLOUCESTERSHIRE HOSPITALS NHS FOUNDATION TRUST, Cheltenham (GB)

(72) Inventors: John Charles Clifford Day, Bristol (GB); Nicholas Stone, Gloucestershire (GB)

(73) Assignees: The University of Bristol, Bristol (GB); GLOUCESTERSHIRE HOSPITALS NHS FOUNDATION TRUST, Cheltenham (GB)

(*) Notice: Subject to any disclaimer, the term of this patent is extended or adjusted under 35 U.S.C. 154(b) by 579 days.

(21) Appl. No.: 16/685,307

(22) Filed: Nov. 15, 2019

(65) Prior Publication Data

US 2020/0085308 A1   Mar. 19, 2020

Related U.S. Application Data

(63) Continuation of application No. 15/346,265, filed on Nov. 8, 2016, now abandoned, which is a (Continued)

(30) Foreign Application Priority Data

Oct. 31, 2011 (GB) ..................... 1118773

(51) Int. Cl.
  *A61B 5/00* (2006.01)
  *A61B 10/00* (2006.01)

(52) U.S. Cl.
  CPC .......... *A61B 5/0086* (2013.01); *A61B 5/0075* (2013.01); *A61B 5/0084* (2013.01);
  (Continued)

(58) Field of Classification Search
  CPC ............... A61B 5/0075; A61B 5/6848; A61B 2562/228; A61B 2560/0443; A61B 5/0084; A61B 5/0086
  See application file for complete search history.

(56) References Cited

U.S. PATENT DOCUMENTS 5,280,788 A   1/1994 Janes et al.
6,373,573 B1   4/2002 Jung et al.
(Continued)

FOREIGN PATENT DOCUMENTS

WO   WO-2007/022196 A2   2/2007
WO   WO-2016102681 A1 *  6/2016 ............. A61B 10/02

OTHER PUBLICATIONS

International Search Report for International application No. PCT/GB2012/052531, dated Apr. 25, 2013.
(Continued)

*Primary Examiner* — Colin T. Sakamoto
(74) *Attorney, Agent, or Firm* — Marshall, Gerstein & Borun LLP (57) ABSTRACT

A probe, such as a spectroscopic probe, for enabling a fluid or tissue sample to be tested in situ. The probe includes a conduit, such as a hypodermic needle, that can be inserted into a test subject and a wave coupling arranged to direct electromagnetic radiation, such as light, from an energy source to the sample and/or from the sample to a receiver for analysis. The receiver may comprise a Raman spectroscope. The probe may include a carriage that can be used to move at least some of the optical coupling towards and away from the insertion tip of the conduit. The probe may include a pressure modifier that can be used to draw fluid into or expel fluid from the conduit.

16 Claims, 7 Drawing Sheets

Related U.S. Application Data continuation of application No. 14/347,555, filed as application No. PCT/GB2012/052531 on Oct. 12, 2012, now abandoned.

(52) U.S. Cl.
CPC ........ *A61B 5/6848* (2013.01); *A61B 10/0045* (2013.01); *A61B 2560/0285* (2013.01); *A61B 2560/0443* (2013.01); *A61B 2562/228* (2013.01)

(56) References Cited

U.S. PATENT DOCUMENTS

| | | | |
|---|---|---|---|
| 6,564,087 B1 | 5/2003 | Pitris et al. | |
| 6,876,801 B2 | 4/2005 | Doyle | |
| 2002/0159055 A1 | 10/2002 | Bennett et al. | |
| 2003/0218756 A1 | 11/2003 | Chen et al. | |
| 2006/0036181 A1 | 2/2006 | Treado et al. | |
| 2006/0264745 A1* | 11/2006 | Da Silva | A61B 5/0091 600/434 |
| 2007/0024856 A1 | 2/2007 | Izatt et al. | |
| 2007/0229801 A1 | 10/2007 | Tearney et al. | |
| 2007/0239033 A1* | 10/2007 | Tearney | G01N 21/23 600/407 |
| 2009/0046980 A1* | 2/2009 | Rohlen | A61B 5/0066 385/52 |
| 2009/0093692 A1 | 4/2009 | Hansma | |
| 2009/0131802 A1 | 5/2009 | Fulghum et al. | |
| 2011/0313299 A1 | 12/2011 | Brennan, III | |
| 2012/0116234 A1 | 5/2012 | Farcy et al. | |
| 2012/0191021 A1* | 7/2012 | Sobol | A61B 10/04 606/15 |
| 2019/0388069 A1* | 12/2019 | Weber | A61B 5/6848 |

OTHER PUBLICATIONS

Written Opinion for International application No. PCT/GB2012/052531, dated Apr. 25, 2013.

International Preliminary Report on Patentability for International application No. PCT/GB2012/052531, dated May 6, 2014.

Volynskaya, Zoya, "*Multimodal Spectroscopy: Real-time Diagnosis of Breast Cancer during Core Needle Biopsy,*" Massachusetts Intitute of Technology (Jun. 12, 2010).

Day et al., "A miniature confocal Raman probe for endoscopic use," *Physics in Medicine and Biology* (Nov. 11, 2009).

Haka et al., "Diagnosing breast cancer using Raman spectroscopy: prospective analysis," *Journal of Biomedical Optics* (Sep./Oct. 2009).

Nijssen et al., "Towards oncological application of Raman spectroscopy," *Journal of Biophotonics* (Jan. 23, 2009).

Komachi et al., "Raman probe using a single hollow waveguide," *Optics Letters*, vol. 30 (Nov. 1, 2005).

Šćepanovićet al., "A multimodal spectroscopy system for real-time disease diagnosis," *Review of Scientific Instruments*, (Apr. 17, 2009).

Utzinger et al., "Fiber optic probes for biomedical optical spectroscopy," *Journal of Biomedical Optics*, vol. 8 (Jan. 2003).

\* cited by examiner

PROBE WITH A REMOVABLE TIP

BACKGROUND

During medical examination of a tissue sample it can be beneficial to identify the tissue type and/or disease state thereof.

For example, when cancer is suspected, a patient may have a tumour removed or biopsied and sent for histopathology analyses. Conventional handling involves the tissue undergoing fixation, staining with dyes, mounting and then examination under a microscope for analysis. Typically, the time taken to prepare the specimen is of the order of one day. The pathologist will view the sample and classify the tissue as malignant or benign based on the shape, colour and other cell and tissue characteristics. The result of this manual analysis depends on the choice of stain, the quality of the tissue processing and staining, and ultimately on the quality of education, experience and expertise of the specific pathologist.

Thus, conventional tissue examination can be surgically invasive, time consuming and the accuracy of a diagnosis may be heavily reliant on human judgement.

SUMMARY

According to a first aspect of the invention, there is provided a probe comprising: an elongate conduit for piercing human tissue, the elongate conduit comprising a first opening and a second opening; a wave coupling for transmitting electromagnetic radiation from an energy source into the conduit and/or transmitting electromagnetic radiation from the conduit to a receiver.

Thus, a probe according to this aspect includes a conduit, such as a needle, via which electromagnetic radiation can be used for examining a tissue sample. The conduit is arranged and configured such that it may easily be inserted into human tissue and as such the probe can be used to test subcutaneous tissue and/or fluid. The probe can be coupled to a receiver that can be used to analyse the electromagnetic radiation returned from the sample through the conduit.

The probe may comprise a carriage for moving an element of the wave coupling between a first, or deployed, condition and a second, or retracted, condition. A portion, such as the tip, of the wave coupling element may be closer to the second opening of the conduit when the wave coupling element is in the deployed condition than it is when wave coupling element is in the retracted condition.

Thus, a probe according to such an embodiment enables the position of the tip or other portion of the wave coupling element to be varied. As such, the tip or other portion may be stowed within the conduit during insertion of the conduit into human tissue or the like, so as to reduce the likelihood of the tip being damaged or coming into contact with subcutaneous fluid or tissue which may impair the wave coupling efficiency of the element. Once the conduit has been inserted to a measurement depth the wave coupling element can be moved to the deployed condition for testing.

The tip or other portion of the wave coupling element may be at, or adjacent, the second opening of the conduit when the wave coupling element is in the deployed condition.

Thus, a probe according to such an embodiment enables the tip of the wave coupling element to be moved to a position in which it is adjacent the tissue at the insertion depth of the conduit. This may improve the testing accuracy of the probe relative to an embodiment where the tip of the element is significantly spaced from the target tissue because the wave coupling transmits the electromagnetic radiation substantially all of the way to the target tissue.

The tip or other portion of the wave coupling element may be spaced from second opening of the conduit when the wave coupling element is in the retracted condition. For example, the tip may be spaced from the second opening by at least: one tenth; one eighth; one quarter; a half; three quarters; or the entire length of the conduit.

Thus, a probe according to such an embodiment enables the tip to be spaced from the tissue insertion end i.e. the second opening of the conduit. Increasing the spacing can provide a more efficient buffer between the second opening and the tip of the wave coupling element. However, there may be a trade-off between providing a suitable buffer spacing and enabling the tip to easily reach a target location, such as the second opening of the conduit.

The wave coupling element may comprise a waveguide. The wave coupling element may comprise a plurality of waveguides. A waveguide may comprise optical fibre.

The carriage may comprise a plunger of a syringe to which the conduit is coupled.

Thus, a probe according to such an embodiment may conveniently make use of a syringe plunger to act as the carriage. The body of the syringe provides a convenient structure to which to attach the conduit.

The probe may include a pressure modifier arranged in fluid communication with the first opening of the conduit, the pressure modifier being operable to change the pressure within the conduit. In some embodiments the pressure modifier may comprise a pump.

Thus, a probe according to such an embodiment includes a pressure modifier which can be used to modify the pressure at the first opening of the conduit to draw fluid into the conduit or expel fluid from the conduit. In embodiments where a tip, or other portion, of a wave coupling element is arranged to be moved to the second opening, it is advantageous to be able to expel fluid, such as saline solution, from the conduit because this may clear the passageway between the tip of the wave coupling element and the target tissue of subcutaneous tissue and fluid that may otherwise inhibit the passage of electromagnetic radiation. In any embodiments which include a pressure modifier, the pressure modifier may be used to administer a therapeutic drug, anaesthetic or the like to a test subject via the conduit. In embodiments where fluid is to be tested, it is advantageous to be able to draw the test fluid into the conduit.

The pressure modifier may comprise a plunger of a syringe to which the conduit is coupled.

Thus, a probe according to such an embodiment may conveniently make use of a syringe plunger to act as the pressure modifier. The body of the syringe provides a convenient structure to which to attach the conduit.

A portion of the wave coupling element which enters the conduit may include a stiffening support, such as a metal or hard plastics coating.

The pressure modifier may be arranged to reduce the pressure within the conduit. The wave coupling may include a lens arranged to focus electromagnetic radiation into the conduit. The conduit may include a reflective layer or region. The reflective region may provide a number of advantages: it may increase the transmission of electromagnetic radiation along the length of the conduit; it may increase the path length and/or collection efficiency of electromagnetic radiation in fluid within the conduit, which may in some embodiments improve the collection efficiency of Raman emission; and it may reduce the likelihood the electromagnetic radiation escaping laterally from the conduit.

Thus, a probe according to such an embodiment may be more accurate and/or sensitive than a system which includes optical fibre alone.

The conduit may comprise a hypodermic needle.

The energy source may comprise a light source, such as a laser.

The electromagnetic radiation may be within the range of ultraviolet to infrared.

In any embodiment of the invention including optical fibre, the fibre may have a diameter of 300 µm or less, preferably 200 µm or less and advantageously 150 µm or less.

The receiver may comprise a spectroscopic detector, such as a detector arranged to detect Raman spectra.

The probe may comprise a body portion and a tip portion arranged to be removably coupled to body portion, wherein the elongate conduit is associated with the tip portion.

Thus, the tip portion, which includes the elongate conduit and in use is likely to be contaminated by test tissue or test fluid, can be uncoupled from the body portion of the probe. As such, the tip portion may be discarded following a single use, but the body portion may be retained for subsequent use.

The wave coupling may include one or more wave manipulation modules associated with the body portion.

Thus, relatively expensive components of the probe such as the wave manipulation modules may be associated with the reusable portion of the probe.

The body portion may include a first wave coupling interface and the tip portion may include a second wave coupling interface, the first and second wave coupling interfaces being arranged to provide wave communication between the first and second portions of the wave coupling when the tip portion is coupled to the body portion.

Thus, the probe may provide an efficient wave interface between the body portion and the tip portion.

The carriage may comprise a body carriage associated with the body portion and a tip carriage associated with the tip portion, the body and tip carriages being arranged to be removably coupled to one another.

Thus, part of the carriage may be reusable. In some embodiments, wave manipulation modules, such as light manipulation modules, may be associated the reusable part of the carriage.

A portion of the pressure modifier which is arranged to be in fluid communication with the elongate conduit may be associated with the tip portion.

Thus, part of the pressure modifier may be reusable.

According to a second aspect of the invention, there is provided an optical spectroscope including a probe according to the first aspect. The optical spectroscope may comprise a Raman or fluorescence spectroscope.

According to a third aspect of the invention, there is provided a method of testing a tissue or fluid sample comprising the steps of: inserting the conduit of a probe according to the first aspect into the tissue of a test subject; and either transmitting electromagnetic radiation to the tissue or fluid sample via the wave coupling or transmitting electromagnetic radiation from the tissue or fluid sample to a receiver via the wave coupling.

The method may comprise moving an element of the wave coupling, such as the tip thereof, from a retracted condition to a deployed condition once the conduit has been inserted into the tissue of the test subject.

The method may comprise modifying the pressure at the first opening of the conduit while the probe is inserted in the tissue of the test subject to expel fluid into the test subject or to draw fluid from the test subject into the conduit. The method may comprise the step of administering a therapeutic drug, anaesthetic or the like to the test subject via the conduit.

BRIEF DESCRIPTION OF THE DRAWINGS

Embodiments of the invention will now be described with reference to the accompanying drawings, in which:

FIG. 1b is a diagram in cross section through A-A of the probe of FIG. 1a;

FIG. 2b is a view in cross section through A-A of the probe of FIG. 2a;

FIG. 3 is a diagram of the optical coupling of the probe of FIG. 1a;

DETAILED DESCRIPTION

Figure 1A:
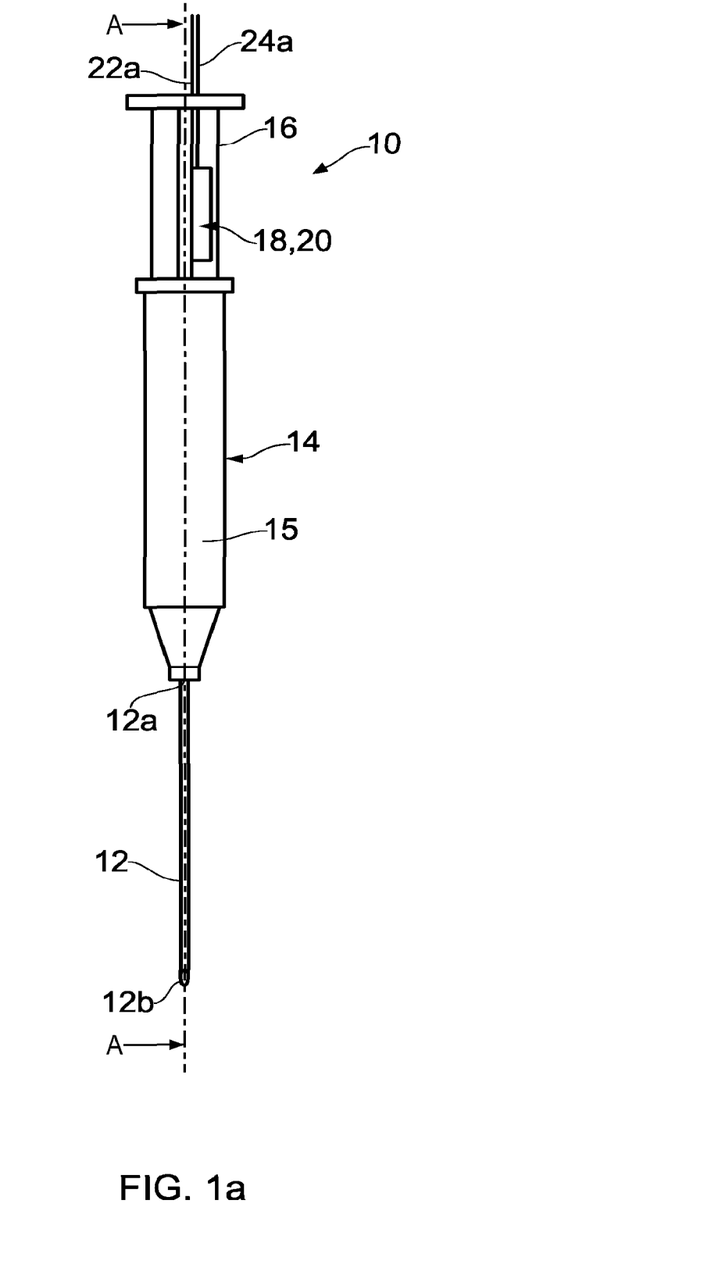
FIG. 1a is a diagram of a probe according to a first embodiment of the invention, showing the wave coupling element in a retracted condition.
Figure 1B:
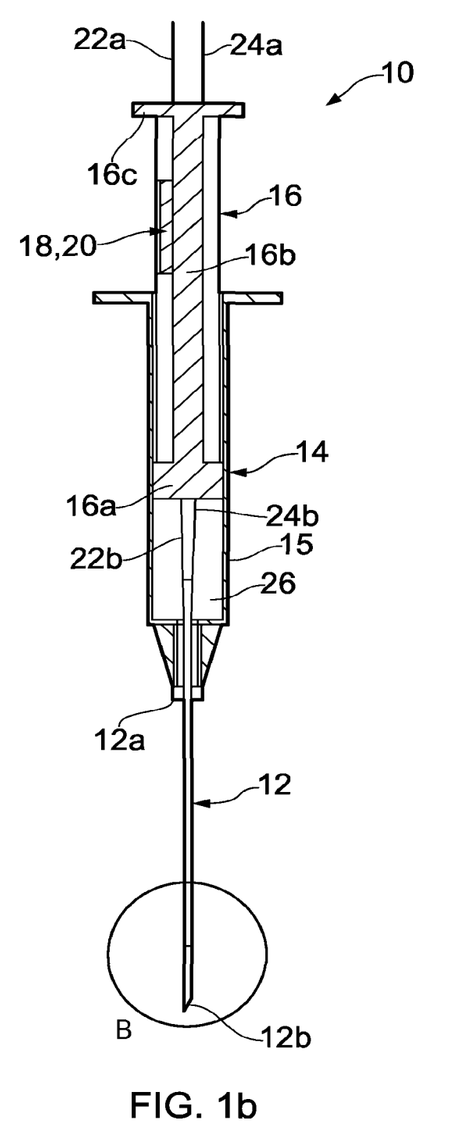
Figure 1C:
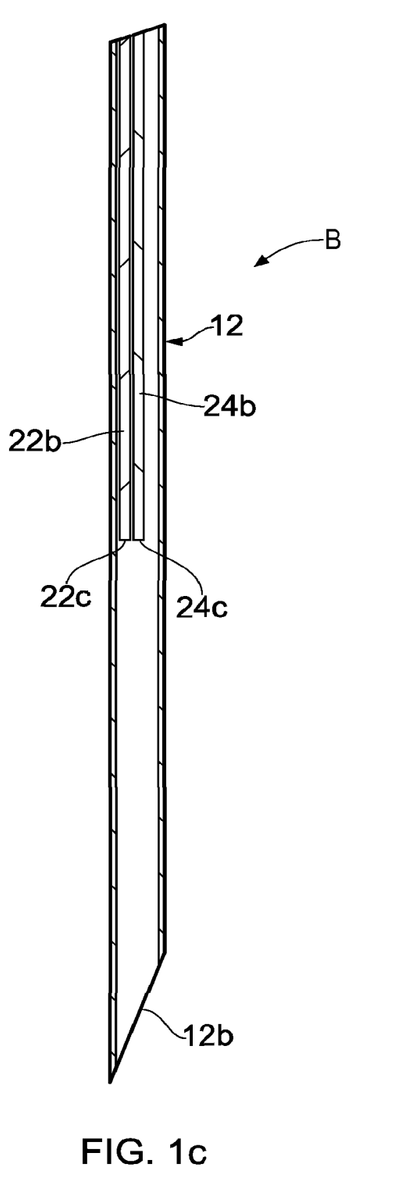
FIG. 1c is an enlarged view of the tip region B of the probe of FIG. 1b.

FIGS. 1a to 1c show a probe 10 according to a first embodiment of the present invention. The term "probe" is used in relation to embodiments of the invention to mean an instrument, such as a surgical instrument, which is suitable for, or arranged to be, at least partially inserted into human or animal tissue to enable a fluid or tissue sample to be tested in situ using electromagnetic radiation such as light.

The probe 10 according to embodiments of the invention enables subcutaneous tissue to be tested using spectroscopy, preferably Raman spectroscopy. As will be understood, when exciting optical energy of a single wavelength interacts with a molecule, the optical energy scattered by the molecule may contain small amounts of optical energy having wavelengths different from that of the incident exciting optical energy. This is known as the Raman effect. The wavelengths present in the scattered optical energy are characteristic of the structure of the molecule, and the intensity of this optical energy is dependent on the concentration of these molecules. Thus, the identities and concentrations of various molecules in a substance can be determined by illuminating the substance with energy of a single wavelength and then measuring the individual wavelengths, and their intensities, in the scattered optical energy. Raman spectroscopy provides a means for obtaining similar molecular vibrational spectra over optical fibres using visible or near infrared light that is transmitted by the optical fibres without significant absorption losses. In Raman spectroscopy, monochromatic light is directed to a sample and the spectrum of the light scattered from the sample is determined. It should however be noted that a probe according to embodiments of the invention may be used with any suitable receiver or detector, such as a spectroscopic detector arranged to measure fluorescence or elastic scattering.

The probe 10 generally comprises an elongate conduit 12 which is arranged to pierce human tissue, a wave coupling 18, 20, 22a, 22b, 24a, 24b arranged to transmit electromagnetic radiation from an energy source (not shown) into the conduit 12 and/or transmit electromagnetic radiation from the conduit 12 to a receiver (not shown), a carriage 16 for moving an element 22b, 24b of the wave coupling between a deployed condition and retracted condition and a pressure modifier 16 arranged in fluid communication with the conduit 12, the pressure modifier 16 being operable to change the pressure within the conduit 12.

The elongate conduit 12 has a first opening 12a and a second opening 12b. The openings 12a, 12b are spaced from one another at opposite ends of the conduit 12. The conduit 12 is hollow so as to define a fluid passageway between the openings 12a, 12b such that the openings 12a, 12b are in exclusive fluid communication with one another via the conduit 12. A proximal end of the conduit 12 is connected to the body of a syringe 14 so as to provide a fluid-tight coupling therewith via the first opening 12a. A distal end of the conduit 12 defines a tip which is arranged and configured to enable the conduit to pierce human tissue or the like. For example, the conduit tip may define a sharp point such as that of a hypodermic needle. The second opening 12b is located at the tip of the conduit 12. The conduit 12 is formed of a resilient material such as steel. The conduit 12 may have an outer diameter which is less than 2 mm, 1.5 mm or less than 1 mm. Preferably, the conduit has an outer diameter which is equal to or less than 0.95 mm. In some embodiments the conduit may comprise a conventional hypodermic needle, such as a 20 gauge needle. The conduit 12 may have any suitable length, such as less than or equal to: 300 mm, 200 mm or 100 mm.

The wave coupling 18, 20, 22a, 22b, 24a, 24b in the illustrated embodiment is an optical coupling and comprises: an input light guide 22a, such as optical fibre, via which laser light may be transmitted from a laser (not shown); a first light manipulation module 18 (which is described in more detail with reference to FIG. 3); an excitation light guide 22b, such as optical fibre, via which the manipulated laser light may be directed into the conduit to a sample to be tested, such as tissue or fluid; a collection light guide 24b, such as optical fibre, via which light collected from the sample may be transmitted; a second light manipulation module 20 (which is described in more detail with reference to FIG. 2) arranged to manipulate the light returned from the sample; and an output light guide 24a, such as optical fibre, via which light exiting the second light manipulation stage 18 may be transmitted to a receiver, such as a spectrometer.

As will be appreciated, the exact configuration of the wave coupling according to embodiments of the invention will depend on factors such as the type of electromagnetic radiation used, the target sample and the type of receiver used. In embodiments of the invention the wave coupling may comprise any suitable waveguides and manipulation modules. In some embodiments the probe may include just an excitation path or just a return path, but not both. Thus, two probes could be used together, with one providing the excitation radiation and the other transmitting the radiation from the sample to the receiver. This may enable the probes to be used for spatially offset Raman spectroscopy and/or transmission measurements.

In the illustrated embodiment, the wave coupling element 22b, 24b consists of the excitation light guide 22b and the collection light guide 24b, which are connected to one another to improve the stiffness of the wave coupling element 22b, 24b. The close proximity of the light guides 22b, 24b forming the wave coupling element 22b, 24b may provide for particularly efficient collection of light from the sample, such as Raman scattered light. While only a single excitation light guide 22b and a single collection light guide 24b are shown, there may in other embodiments be a plurality of either. The wave coupling element 22b, 24b, or components thereof, may be clad with a metal coating or jacket to improve the stiffness of the wave coupling element 22b, 24b. The tip 22c, 24c of each light guide forming the wave coupling element 22b, 24b may be configured to provide a substantial overlap between the illuminating and the collection cone. For example, the tip 22c of the excitation light guide 22b and the tip 24c of the collection light guide 24b may be polished to an angle of approximately 30° from the longitudinal axis thereof, the two angled faces converging to define a point. This configuration causes the laser excitation to be emitted towards the collection light guide 24b and the acceptance cone of the collection light guide 24b to be angled towards the illuminating spot.

In other embodiments, the wave coupling element may comprise any part of the wave coupling.

In the illustrated embodiment, the carriage 16 for moving the wave coupling element 22b, 24b between the deployed and retracted conditions comprises a plunger 16 of the syringe 14. The plunger 16 is conventional in that it has a body 16b having a piston seal 16a at one end which is contained within the barrel 15 of the syringe 14 and an enlarged base 16c which protrudes from the barrel 15 of the syringe 14 and may be used to actuate the plunger 16. The light manipulation modules 18, 20 are mounted on the plunger body 16b. Consequently, movement of the plunger 16 causes corresponding movement of the wave coupling element 22a, 22b.

The syringe 14 defines a pressure modifier arranged in exclusive fluid communication with the first opening 12a of the conduit 12, the pressure modifier being operable to change the pressure at the first opening 12a of the conduit 12. Thus, a probe 10 according to such an embodiment includes a pressure modifier which can be used to modify the pressure within the conduit 12 to draw fluid into the conduit 12 or expel fluid from the conduit 12. In embodiments where a tip, or other portion, of the wave coupling element 22b, 24b is arranged to be moved to the second opening 12b, it is advantageous to be able to expel fluid, such as saline solution, from the conduit 12 because this may clear the passageway between the tip of the wave coupling element 22b, 24b and the target tissue of subcutaneous tissue and/or fluid that may inhibit the passage of electromagnetic radiation. In some embodiments the optical coupling between the probe and tissue may also be improved. In embodiments where fluid is to be tested (as described in more detail with reference to FIG. 4), it is advantageous to be able to draw the test fluid into the conduit 12. Thus, the probe 10 according to the illustrated embodiment conveniently makes use of a syringe plunger 16 to act as the pressure modifier and carriage. The body of the syringe 15 provides a convenient structure to which to attach the conduit.

In other embodiments which include a carriage for moving one or more portions of the wave coupling, the carriage may be any suitable part arranged to move relative to the conduit of the probe and should the embodiment also include a pressure modifier, the carriage need not also serve as the pressure modifier. For example, the plunger 16 of the illustrated embodiment may include an opening, or one way valve, through the piston seal 16a such that the plunger can be depressed without forcing fluid into the conduit 12. Although the plunger of such an embodiment may affect the pressure within the conduit 12, it is not arranged to modify the pressure in the conduit such that a substantial quantity of fluid can be drawn into, or purged from, the conduit and thus is not considered to be a pressure modifier as disclosed herein. A substantial quantity in embodiments of the invention may be at least 5%, 10%, 20%, 30%, 40%, 50%, 75% or 100% of the volume of the conduit chamber 12d.

In other embodiments which include a pressure modifier arranged to change the pressure within the conduit 12, the pressure modifier may be any suitable part arranged to increase or decrease the pressure at an opening of the probe 12. Should an embodiment include a carriage and a pressure modifier, the pressure modifier need not also serve as the carriage. For example, the optical coupling may be coupled to the syringe body of the illustrated embodiment and the plunger 16 may move relative to both the syringe body and optical coupling as is the case with the embodiment described with reference to FIG. 4. In some embodiments the pressure modifier may comprise a pump.

Figure 3:
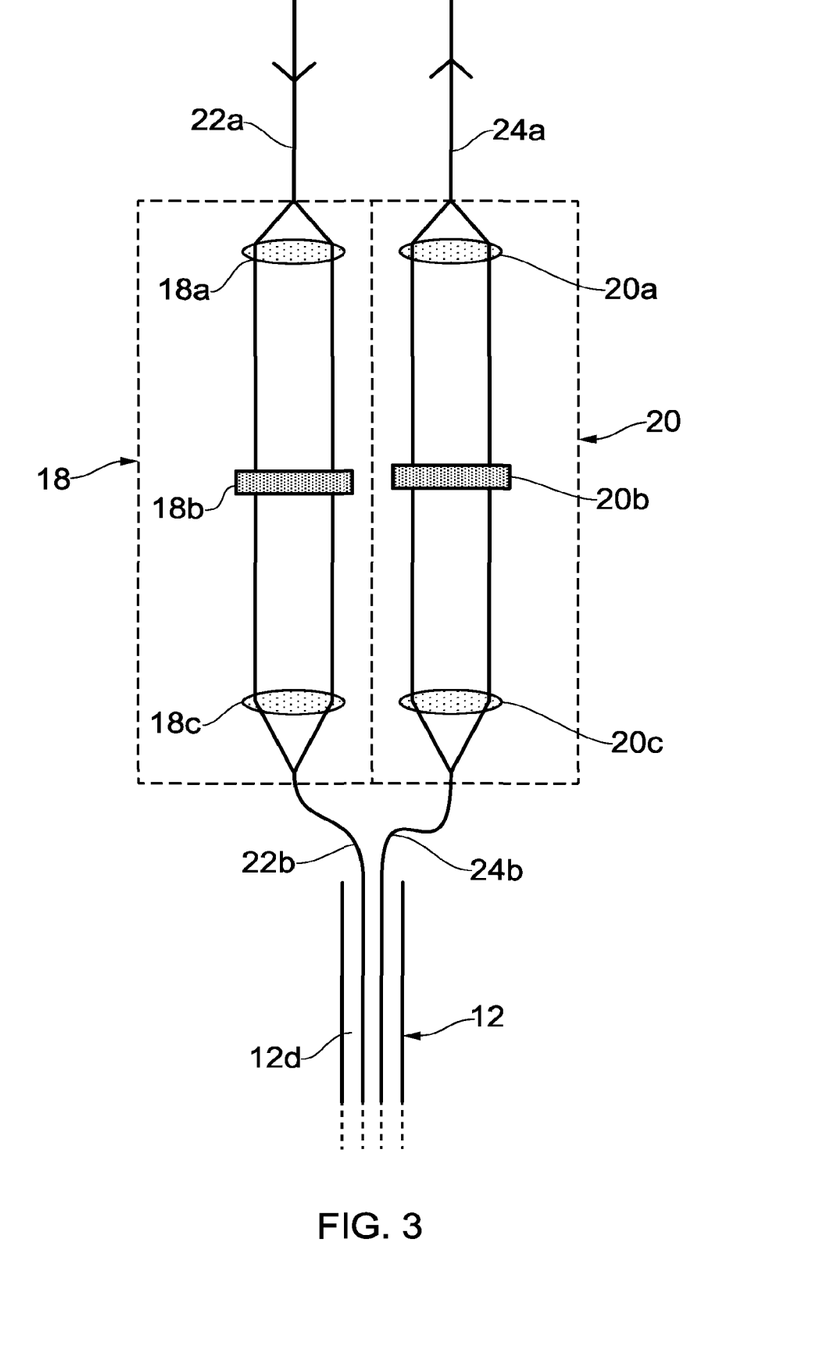

Referring additionally to FIG. 3, the light manipulation modules 18, 20 are shown in more detail. The input light guide 22a, which in this embodiment is arranged to be coupled to a laser light source, directs laser light into a gradient index (GRIN) input lens 18a. The input lens 18a collimates the laser light to generate a collimated beam. The collimated beam is then passed through a short wavelength pass filter 18b that rejects Raman and photoluminescence emission generated within the input light guide 22a. The filtered light is then passed to a GRIN focussing lens 18c. The focussing lens 18c focus the filtered light into the excitation light guide 22b which transmits the filtered light into the conduit 12 to the target sample.

Light from the sample is collected and collimated by a GRIN collecting lens 20c and directed to a long wavelength pass filter 20b that rejects the laser excitation light. Stokes shifted wavelengths are transmitted by the filter 20b. The filtered light is then focussed by a GRIN output lens 20a into the output light guide 24a which is arranged to be coupled to a receiver, such as a spectrometer for generating a Raman spectrum.

In other embodiments, any suitable electromagnetic radiation may be used as the excitation signal. It should be also noted that, while GRIN lenses have been described, any suitable lens type may be used in the optical coupling of other embodiments.

In the illustrated embodiment, the tip 22c, 24c of the wave coupling element 22b, 24b is closer to the second opening 12b of the conduit 12 when the wave coupling element 22b, 24b is in the deployed condition than when wave coupling element 22b, 24b is in the retracted condition. Thus, the probe 10 enables the position the tip 22c, 24c of the wave coupling element 22b, 24b to be varied. As such, the tip 22c, 24c may be stowed within the conduit 12 during insertion of the conduit 12 into human tissue or the like, so as to reduce the likelihood of the tip 22c, 24c being damaged or coming into contact with subcutaneous fluid or tissue which may otherwise impair the wave transmitting efficiency of the wave coupling. Once the conduit 12 has been inserted to a measurement depth, the wave coupling element 22b, 24b can be moved to the deployed condition for testing. When in the deployed condition, the tip 22c, 24c of the wave coupling element 22b, 24b may be in contact with the tissue sample.

As shown in FIGS. 1b and 1c, the tip 22c, 24c of the wave coupling element 22b, 24b is spaced from second opening 12b of the conduit 12 when the wave coupling element 22b, 24b is in the retracted condition. For example, the tip 22c, 24c may be spaced from the second opening 12b by at least: one tenth of; one eighth of; one quarter of; a half of; three quarters of; or the entire length of the conduit 12. Thus, a probe 10 according to such an embodiment enables the tip 22c, 24c of the wave coupling element 22b, 24b to be spaced from the second opening 12b of the conduit 12. Increasing this spacing can provide a more efficient buffer between the second opening 12b and the tip 22c, 24c of the wave coupling element 22b, 24b. However, there may be a trade-off between providing a suitable buffer spacing and enabling the tip 22c, 24c to easily reach a target location, such as the second opening 12b of the conduit 12. In embodiments which include a pressure modifier, it may be desirable for the tip 22c, 24c of the wave coupling element 22b, 24b to be spaced from the second opening 12b of the conduit 12 by less than one quarter of the length of the conduit 12 so as to limit the volume of fluid that is displaced as the wave coupling element 22b, 24b moves between the retracted and deployed configurations.

Figure 2A:
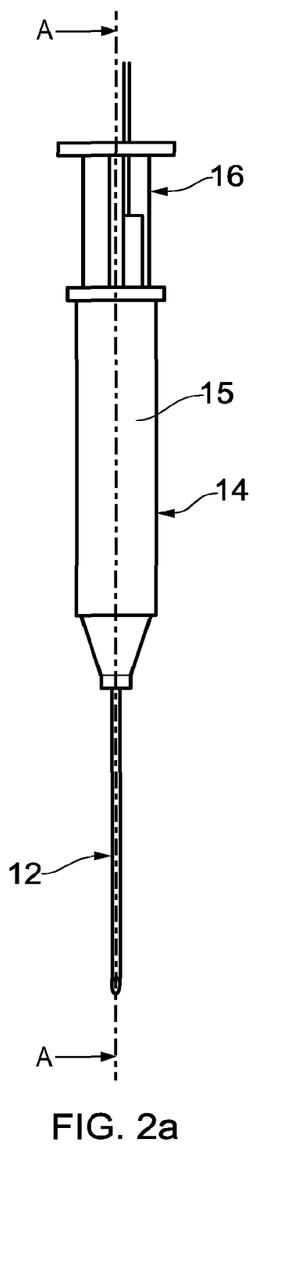
FIG. 2a is a diagram of the probe of FIG. 1a showing the wave coupling element in a deployed condition.
Figure 2B:
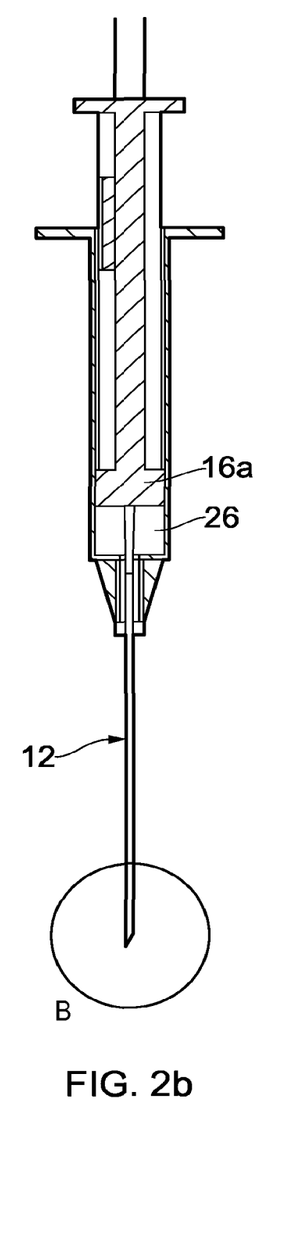
Figure 2C:
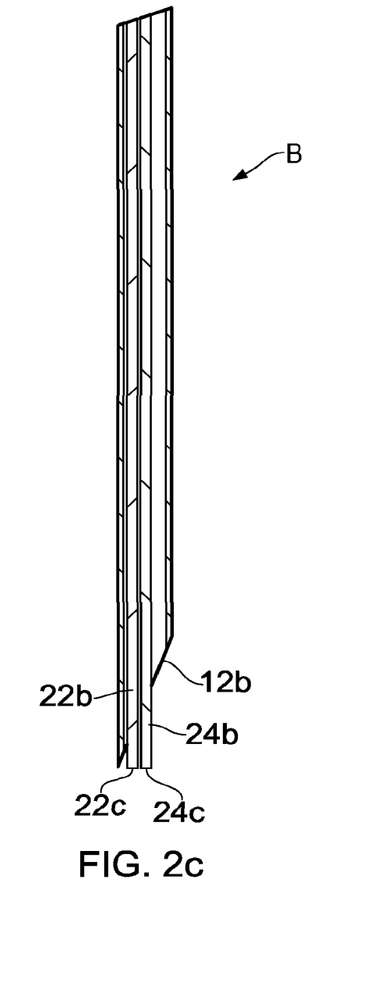
FIG. 2c is an enlarged view of the tip region B of the probe of FIG. 2b.

Referring additionally to FIGS. 2a to 2c, the tip 22c, 24c of the wave coupling element 22b, 24b is positioned at the second opening 12b of the conduit 12 when the wave coupling element 22b, 24b is in the deployed condition. This enables the conduit 12 to be inserted into tissue to a required measurement depth and the tip 22c, 24c of the wave coupling element 22b, 24b brought close to the tissue to be sampled. This may improve the testing accuracy of the probe 10 relative to an embodiment where the tip 22c, 24c of the element 22b, 24b is significantly spaced from the target tissue because the wave coupling of the probe 10 transmits the electromagnetic radiation substantially all of the way to and from the target tissue. Arranging the probe such that the tip 22c, 24c of the wave coupling element contacts the tissue sample when in the deployed condition may advantageously remove the need for a lens at the tip and/or remove the need for setting a focal distance.

Figure 4:
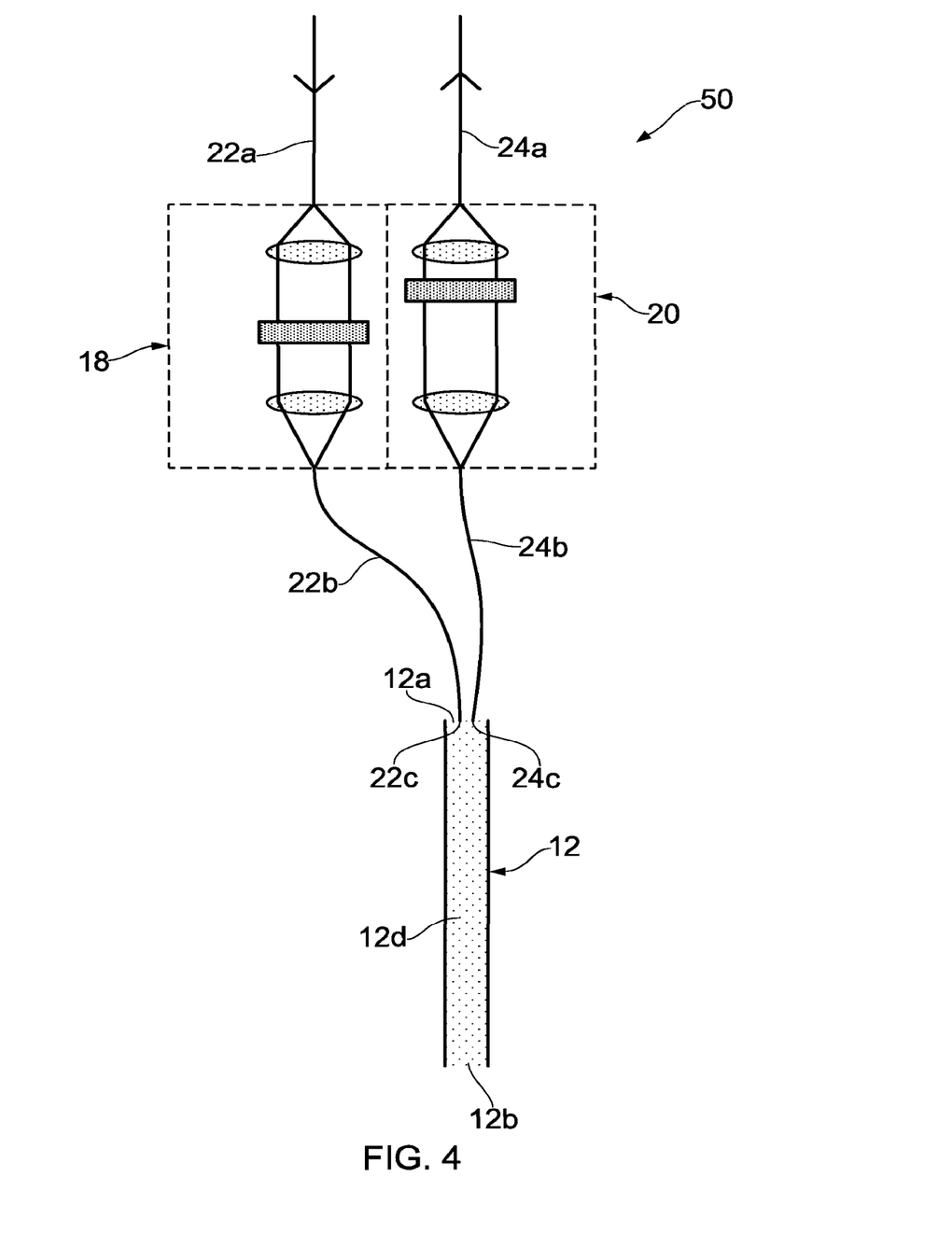
FIG. 4 is a diagram of a probe according to a second embodiment of the invention.

FIG. 4 shows a probe 50 according to a further embodiment of the present invention. The probe 50 according to this embodiment is similar to the probe 10 according to the first embodiment and as such, for brevity, the following description will focus on the differences between them. Corresponding parts have been given the same reference numerals.

The probe 50 is arranged for a fluid sample to be tested within the chamber 12d of the conduit 12. The conduit 12 is coupled to a syringe such as the syringe 14 of the first embodiment (which, for clarity, is not shown). However, in this embodiment the wave coupling 18, 20, 22a, 22b, 24a, 24b is mounted so as not to move relative to the conduit 12. The plunger of the syringe defines a pressure modifier arranged to reduce the pressure within the conduit 12 such that sample fluid can be drawn into the conduit cavity 12d for testing. The tip 22c, 24c of the wave coupling element 22b, 24b is provided adjacent to the first opening 12a of the conduit 12. Thus, excitation light is emitted into the conduit cavity 12d and through the fluid sample therein. Light from the sample is collected and transmitted to a receiver. Alternatively, the tip 22c, 24c of the wave coupling element 22b, 24b may be provided inside the conduit 12 as this may increase the likelihood of the excitation radiation emerging into the sample fluid, rather than encountering a buffer fluid or the like inside the conduit chamber 12d.

The conduit 12 may include a reflective region which extends along the conduit 12 arranged such that light undergoes substantially total internal reflection at the conduit surface. The reflective region may comprise a reflective coating, a polished surface, a sheath of a reflective material, or the like. In some embodiments the reflective region comprises a low refractive index polymer coating. Providing a reflective region may advantageously increase the path length of the radiation in fluid within the chamber 12*d* of the conduit 12, which may improve the collection efficiency of Raman emission and/or luminescence present within fluid within the conduit 12. Providing a reflective region may also reduce the likelihood the electromagnetic radiation escaping laterally from the conduit 12 and may increase the transmission efficiency.

In another embodiment of a probe arranged for a fluid sample to be tested within the chamber 12*d* of the conduit 12, the wave coupling may include an objective lens arranged to focus electromagnetic radiation into the conduit 12. The objective lens may replace the wave coupling element 22*b*, 24*b* shown in FIG. 4. A probe according to such an embodiment may be more accurate than a probe which includes optical fibre, for reasons which will be apparent to the skilled person.

In any embodiment of the invention, the electromagnetic radiation may be within the range of ultraviolet to infrared.

In any embodiment of the invention including optical fibre, the fibre may have a diameter of 300 µm or less, preferably 200 µm or less and advantageously 150 µm or less.

Figure 5:
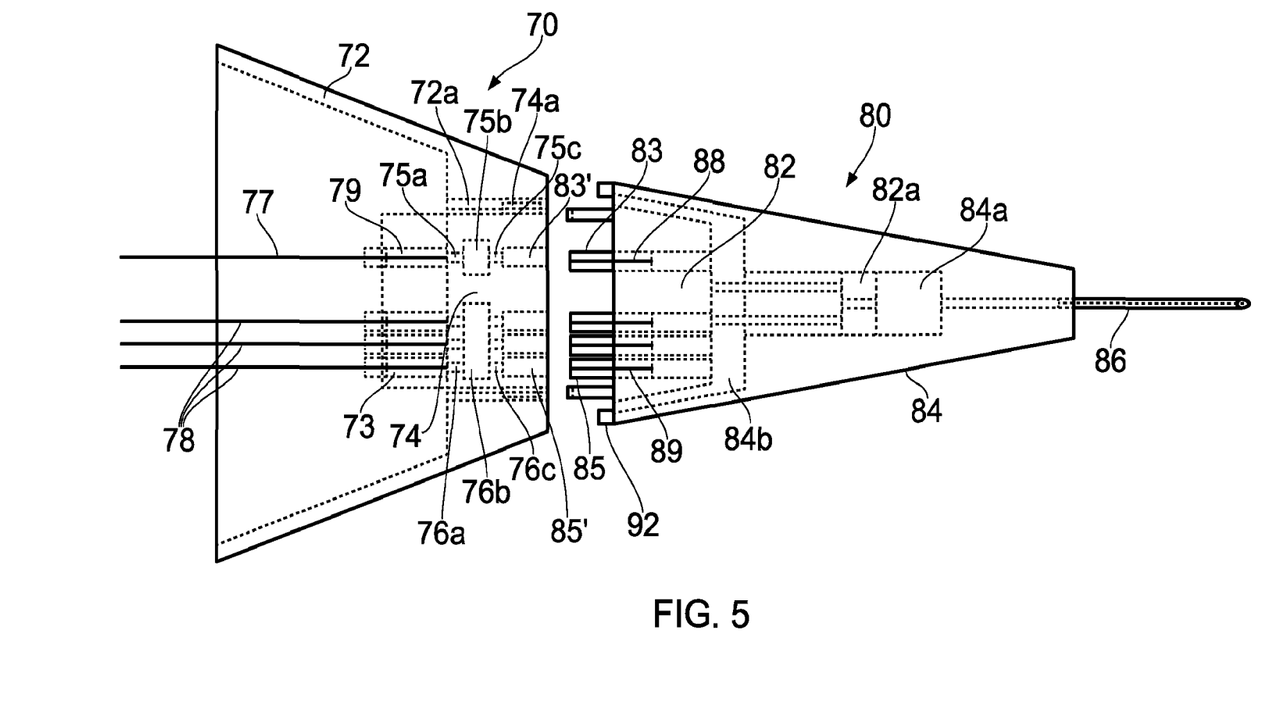
FIG. 5 is a diagram of a probe according to a third embodiment of the invention, shown in an uncoupled condition.

FIG. 5 shows a probe 60 according to a third embodiment of the invention. The wave coupling 77, 78, 75, 76, 88, 89 in the illustrated embodiment is an optical coupling. The probe 60 is similar to the probe 10 of the first embodiment; as such, for brevity, the following description will focus on the differences therebetween. The comments made above in relation to the probe 10 of the first embodiment and/or the probe 50 of the second embodiment may apply equally to the probe 60 according to the third embodiment.

The probe 60 has a body portion 70 and a tip portion 80 that are arranged to be removably coupled to one another. Thus, the tip portion 80 may be disposed following a single use, but the body portion 70 may be reusable.

The body portion 70 includes a fixed body 72 and a movable body carriage 74.

The fixed body 72, of which only a part is shown in FIG. 5, includes a handle (not shown) for a user to grasp the probe 60. The fixed body 72 is in a fixed spatial relationship with the handle.

The body carriage 74 is movably coupled to the fixed body 72; for example, body 72 may define a channel having a plurality of guide track 72*a* extending axially along the wall(s) defining the channel, each guide track 72*a* being arranged to slidably receive a rib 74*a* protruding from the body carriage 74. The body portion 70 may be arranged such that a user grasping the handle of the fixed body 72 can move the body carriage 74 relative to the fixed body 72; for example, the body carriage 74 may include a contact surface that the user can push and/or pull to move the body carriage 74. In some embodiment the body portion 70 may include actuation means, such as a trigger or lever driven ratchet mechanism. In the illustrated embodiment the probe 60 handset includes a trigger mechanism (not shown) that linearly transposes the body carriage 74 forward and/or back along a movement axis that is parallel with respect to the longitudinal axis of an elongate conduit 86, which is described in more detail below.

The body carriage 74 houses a set of light manipulation modules 75, 76 that are similar to those described with reference to FIG. 3. However, the light manipulation modules 75, 76 in the illustrated embodiment are arranged to be removably coupled to a wave coupling element 88, 89 that is associated with the removable tip portion 80. The term "associated" is used to mean that wave coupling element 88, 89 is part of the tip portion 80 rather than part of the body portion 70, such that following uncoupling of the portions 70, 80, the wave coupling element 88, 89 remains coupled to the tip portion 80.

The tip portion 80 includes a movable tip carriage 82 and a nose casing 84.

The nose casing 84 is arranged to be removably coupled to the fixed body 72 by way of one or more retention clips 92; for example, the retention clips 92 may comprise flexible hooks or barbed structures arranged to mechanically engage with receiving apertures in the body 72. The nose casing 84 is also arranged to mount the elongate conduit 86. The elongate conduit 86 is similar to that described with reference to FIG. 1.

The tip carriage 82 is arranged to be removably coupled to the body carriage 74 by way of one or more retention clips 94; for example, the retention clips 94 may comprise flexible hooks or barbed structures arranged to mechanically engage with receiving apertures in the body carriage 74. The tip carriage 82 is also arranged to mount the wave coupling element 88, 89; thus, a user can move the wave coupling element 88, 89 relative to the elongate conduit 86 between deployed and retracted conditions by moving or actuating the body carriage 74.

Various types of standard ferrules are available. Typically these could be 1 mm diameter glass or 3 mm Ceramic. However, in other embodiments the ferrules may have any suitable size and be formed of any suitable material, such as a ceramic material, plastics material or stainless steel. The fibre may be inserted into the ferrule and cemented with an epoxy or adhesive, or connectors may also use crimped ferrules that do not require cement.

The casing 84 defines a syringe chamber 84*a* arranged to slidably receive a closely fitting plunger 82*a* of the movable tip carriage 82. The casing 84 performs a similar function to the syringe barrel 15 of the first embodiment and likewise the plunger 82*a* performs a similar function to the plunger body 16*b*. Thus, movement of the body carriage 74 can modify the pressure within the elongate conduit 86 to expel or draw fluid within the conduit 86.

The casing 84 also defines working cavity 84*b* arranged to enable the tip carriage 82 to move between deployed and retracted conditions while the casing 84 is coupled to the fixed body 72. The working cavity 84*b* may be vented to atmosphere by a vent (not shown) to enable pressure equalisation during movement of the movable tip carriage 82.

The excitation path of the wave coupling includes a laser fibre 77 that extends from a laser (not shown) into the fixed body 72 and is terminated with a glass or ceramic ferrule 79 that holds the end of the fibre 77 and precisely aligns it to a socket in the body carriage 74. The ferrule 79 is mounted in the body carriage 74 directly behind, and at the focal point of a collimating lens 75*a* of the first light manipulation module 75. The lens 75*a* may be a Grin lens with zero working distance in which case the ferrule 79 and fibre 77 end butt up to the lens 75*a*, but other lenses and working distances may be used in other embodiments. Collimated light from the lens 75*a* passes through a short wavelength pass filter 75*b* to remove Raman or fluorescence generated in the fibre 77. The short wavelength pass filter 75*b* is also mounted in the moveable body carriage 74. The filtered collimated light then passes into a focussing lens 75*c*, similar to the input collimator 75*a*, that focuses the light to a point coincident with the end of an excitation fibre 88 of the wave coupling element 88, 89, when the tip portion 80 is coupled to the body portion 70. The excitation fibre 88 is terminated at the handset end with a ferrule 83 similar to that described above. The ferrule 83 is permanently mounted in the movable tip carriage 82 and locates into a close fitting hole 83' in the moveable fibre carriage 74 such that the end of the excitation fibre 88 is at the focal point of the focussing lens 75c.

Figure 6:
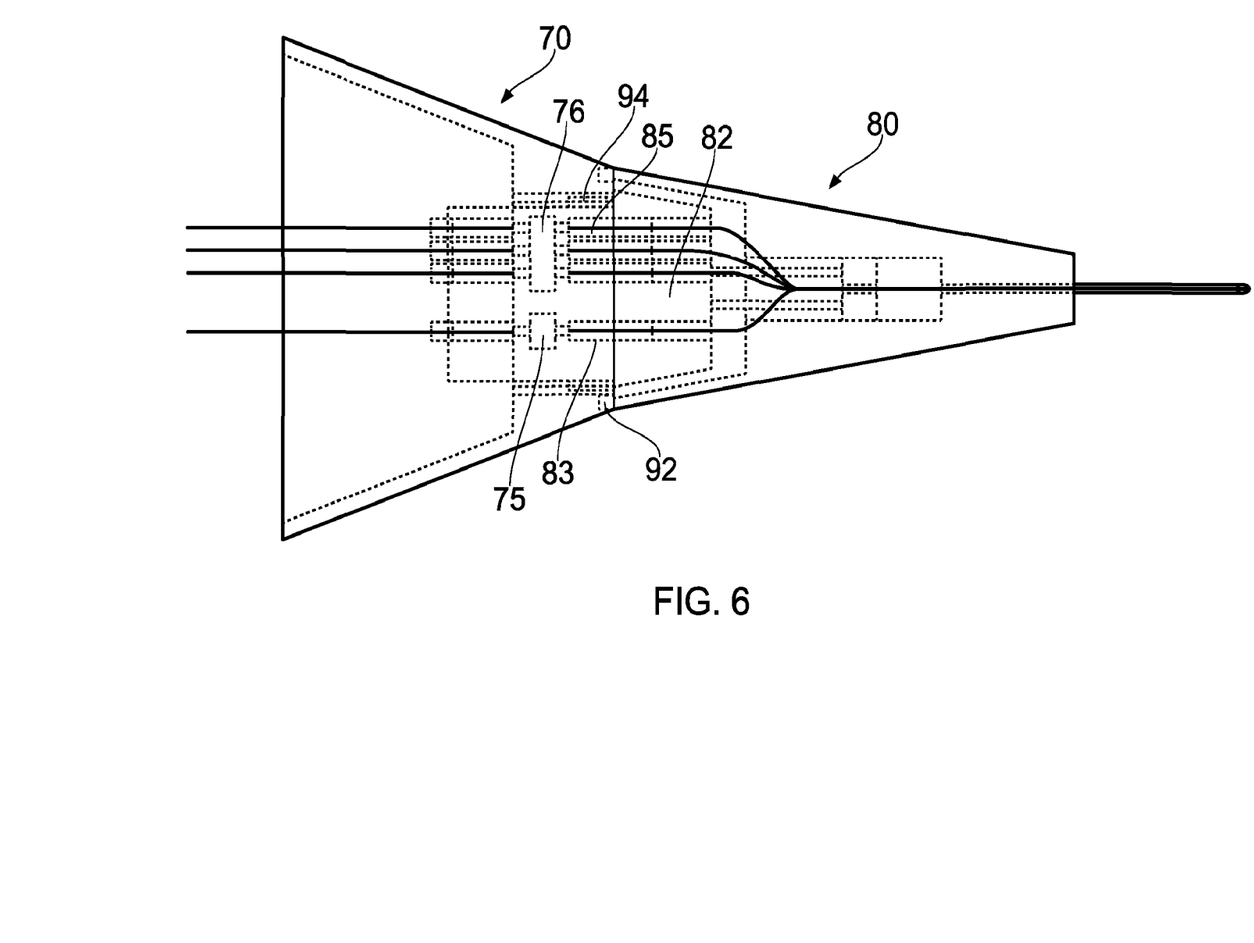
FIG. 6 is a diagram of the probe of FIG. 5, shown in a coupled condition.

The collection path of the wave coupling includes a plurality of collection fibres 89 arranged to collect light from the distal end of the wave coupling element 88, 89 for return to the spectrometer (not shown). The arrangement is similar to that of the laser excitation path but in reverse. Only a short section of excitation and collection fibres 88, 89 are shown in FIG. 5, but in practice the fibres 88, 89 will extend into the elongate conduit 86 as shown in FIG. 6. The collection fibres 89 are each terminated in ferrules 85 permanently mounted in the moveable tip carriage 82. These ferrules 85 locate into close fitting holes 85' in the moveable body carriage 74 such that the fibre 89 ends are at the focal point of the collimating lenses 76c mounted in the body carriage 74. The return path light is collimated by the lenses 76c and passes though a long wavelength pass filter or notch filter 76b that removes light at the laser wavelength. The filter 76b is mounted in the body carriage 74. For each return fibre, the filtered, collimated light hits a respective focussing lens 76a that each focuses the light onto the end of a respective collection fibre 78 mounted in a ferrule 73 which in turn is mounted in the body carriage 74. The collection fibres 78 return the light to the spectrometer for spectral analysis.

The probe 60 according to the illustrated embodiment has a single laser input fibre and a plurality of collection fibres, but in other embodiments may have one or more excitation fibres 88 and one or more collection fibres 89.

In use, a user of the probe 60 may affix the tip portion 80 to the body portion 70 by aligning the two portions such that the ferrules 83, 85 on the tip carriage 82 are aligned with the sockets of the light manipulation modules 75, 76, and the retention clips 92, 94 are respectively aligned, and then pressing the two portions 70, 80 together such that the ferrules 83, 85 enter the sockets and the retention clips 92, 94 respectively engage, as shown in FIG. 6.

The tip portion 80 may be arranged to be applied to the body portion 70 while the wave coupling element 88, 89 is in the retracted condition, such as that shown in FIG. 5; for example, the plunger's 82a resistance to axial movement within the syringe chamber 84a due to the seal therebetween may be greater than the force required to couple the tip portion 80 to the body portion 70.

With the tip portion 80 coupled to the body portion 70, a user may insert the elongate conduit 86 into a tissue sample or the like. Once the distal tip of the elongate conduit 86 is positioned at a desired location, the body carriage 74 can be moved or actuated, thereby moving the tip carriage 82 into the working cavity 84b, moving the plunger 82a along the syringe chamber 84a to expel fluid therefrom, and moving the distal tip of the optical fibre 88, 89 from the retracted condition, in which the tip is shielded within the elongate conduit 86 away from the distal end thereof, to the deployed condition in which the tip is at or adjacent the tip of the elongate conduit 86.

In use, the tip portion 80 may be exposed to tissue sample and fluid sample. As such, it may be desirable to discard the contaminated parts of the probe 60 following use. The probe 60 according to some embodiments advantageously enables the contaminated portion i.e. the tip portion 80 to be removed following use such that it may be discarded, while the body portion 70 may be retained and reused. The body portion according to some embodiments houses the light manipulation modules 75, 76, which are relatively expensive parts of the probe 60.

Although the invention has been described above with reference to one or more preferred embodiments, it will be appreciated that various changes or modifications may be made without departing from the scope of the invention as defined in the appended claims. The word "comprising" can mean "including" or "consisting of" and therefore does not exclude the presence of elements or steps other than those listed in any claim or the specification as a whole. The mere fact that certain measures are recited in mutually different dependent claims does not indicate that a combination of these measures cannot be used to advantage.

The invention claimed is:

1. A Raman spectroscopy probe comprising:
   a body portion having a body coupling face and one or more first coupling elements;
   a tip portion having a tip coupling face and one or more second coupling elements, the first coupling elements being configured to engage with the second coupling elements when the body coupling face is adjacent the tip coupling face to removably couple the tip portion of the probe to the body portion of the probe;
   an elongate, hollow needle having a proximal end attached to the tip portion of the probe and a distal end shaped for piercing human tissue, the needle comprising a first opening at the proximal end and a second opening at the distal end;
   a optical link for transmitting light signals from a light source, though the body portion of the probe and into the needle, and for transmitting light signals from the needle, through the body portion of the probe to a receiver, the optical link comprising:
      a body link section mounted in or on the body portion of the probe, the body link section having a light input for optically coupling to the light source and an end defining a first optical interface; and
      a tip link section mounted in or on the tip portion of the probe, the tip link section having a first end defining a second optical interface and a second end defining a measurement end via which light is emitted and collected, the first and second optical interfaces being arranged to provide optical communication between the body link section and the tip link section of the optical link when the tip portion of the probe is coupled to the body portion of the probe; and
   a carriage for moving the measurement end of the optical link between a deployed condition and a retracted condition, wherein the measurement end is closer to the second opening of the needle when the measurement end is in the deployed condition than it is when measurement end is in the retracted condition,
   the carriage comprising:
      a body carriage movably mounted within the body portion of the probe to move relative to an outer part of the body portion of the probe; and
      a tip carriage movably mounted within with the tip portion of the probe to move relative to an outer part of the tip portion of the probe.

2. A probe according to claim 1, wherein the body carriage comprises a body carriage coupling face and one or more third coupling elements and the tip carriage comprises a tip carriage coupling face and one or more fourth coupling elements, the third coupling elements being configured to engage with the fourth coupling elements when the body coupling face is adjacent the tip coupling face to removably couple the tip carriage to the body carriage.

3. A probe according to claim 1, wherein the body link section of the optical link comprises one or more optical filters located at or adjacent to the first optical interface.

4. A probe according to claim 1, wherein the first optical interface comprises one or more sockets and the second optical interface comprises one or more ferrules sized and disposed to be received within the sockets when the tip portion of the probe is coupled to the body portion.

5. A probe according to claim 1, arranged such that the measurement end of the light transmission link is at, or adjacent, the second opening of the needle when in the deployed condition.

6. A probe according to claim 1, arranged such that the measurement end of the light transmission link is spaced from second opening of the needle when in the retracted condition.

7. A probe according to claim 1, wherein the tip portion includes a tip cavity within which the tip carriage is movable mounted.

8. A probe according to claim 7, wherein the tip cavity includes a bore in fluid communication with the first opening of the needle and the tip carriage comprises a plunger portion arranged to sealingly move along the bore to move fluid between the bore and needle.

9. A probe according to claim 1, wherein a portion of the optical link which enters or is within the needle includes a stiffening support.

10. A probe according to claim 1, wherein the optical link includes a lens arranged to focus light into the needle.

11. A probe according to claim 1, wherein the needle includes a reflective region.

12. A probe according to claim 1, wherein the needle comprises a hypodermic needle.

13. A probe according to claim 1, wherein the light source emits light within a range of ultraviolet to infrared.

14. A probe according to claim 1, wherein the optical link includes at least one excitation optical fibre pathway for transmitting light signals from the light source, though the body portion and into the needle and one or more collection optical fibre pathways for transmitting light signals from the needle, through the body portion to a receiver.

15. A probe according to claim 14, wherein the at least one excitation optical fibre pathway is distinct from the one or more collection optical fibre pathways.

16. A Raman spectroscopy system comprising a probe according to claim 1.

* * * * *